United States Patent [19]

Pletka et al.

[11] 4,222,930
[45] Sep. 16, 1980

[54] SULFUR AND PHOSPHORUS CONTAINING ORGANOSILICON COMPOUNDS AND PROCESS FOR THEIR PRODUCTION AND USE

[75] Inventors: Hans-Dieter Pletka, Mobile, Ala.; Gerd Zezulka, Hanau, Fed. Rep. of Germany

[73] Assignee: Deutsche Gold- und Silber-Scheideanstalt vormals oessler, Frankfurt, Fed. Rep. of Germany

[21] Appl. No.: 967,577

[22] Filed: Dec. 8, 1978

Related U.S. Application Data

[62] Division of Ser. No. 859,968, Dec. 12, 1977, Pat. No. 4,152,347.

[30] Foreign Application Priority Data

Dec. 23, 1976 [DE] Fed. Rep. of Germany ....... 2658368

[51] Int. Cl.² ............................................. C08K 9/06
[52] U.S. Cl. ................................................ 260/42.15
[58] Field of Search ................................... 260/42.15

[56] References Cited

U.S. PATENT DOCUMENTS 3,697,474  10/1972  Morris et al. ..................... 260/42.15
3,949,140  4/1976  Biefeld et al. ..................... 260/42.15

FOREIGN PATENT DOCUMENTS 1254590  5/1973  Fed. Rep. of Germany .
2161943  7/1973  France .

OTHER PUBLICATIONS

Union Carbide; Silane Coupling Agents in Mineral-Reinforced Elastomers; 9/77.
Union Carbide; Silicones, Product Information Bulletin; 1/65.

*Primary Examiner*—Lewis T. Jacobs
*Attorney, Agent, or Firm*—Cushman, Darby & Cushman

[57] ABSTRACT

There are prepared compounds of the formula $$[R_n^1(R^2O)_{3-n}-Si-Alk-S-]_xZ \qquad (I)$$

where
Z is $\equiv$PO, $\equiv$PS, $\equiv$P, $=$PR, $-$P(R)$_2$, $-$P(OR)$_2$, $=$P(OR), $-$PO(OR)$_2$, $-$PS(OR)$_2$, $=$PO(OR) or $=$PS(OR) where R is an alkyl group of 1 to 5 carbon atoms, phenyl or o-, m- or p-nitrophenyl;
Alk is an alkylene group with 2 to 4 carbon atoms;
$R^1$ is an alkyl group having 1 to 5 carbon atoms, benzyl or phenyl;
$R^2$ is an alkyl group having 1 to 5 carbon atoms, a cycloalkyl group having 5 to 8 carbon atoms, phenyl, benzyl or 2-methoxyethyl, each $R^1$ and $R^2$ can have the same or different meanings;
n is 0, 1 or 2; and,
x is 1, 2 or 3, being the residual valence of Z.

The compounds are useful as reinforcing agents in vulcanizable rubber mixtures which contain a silicate filler and optionally carbon black.

17 Claims, No Drawings

SULFUR AND PHOSPHORUS CONTAINING ORGANOSILICON COMPOUNDS AND PROCESS FOR THEIR PRODUCTION AND USE

This is a division of application Ser. No. 4,152,347, issued May 1, 1979.

SUMMARY OF THE INVENTION

This invention relates to chemical compounds containing phosphorus-sulphur and silicon-oxygen-carbon bonds and corresponding to the general formula $$[R_n^1(R^2O)_{3-n}-Si-Alk-S-]_xZ \quad (I)$$

in which

Z has the meanings $=PO$, $=PS$, $\equiv P$, $50$ PR, $-PR_2$, $-P(OR)_2$, $=P(OR)$, $-PO(OR)_2$, $-PS(OR)_2$, $=PO(OR)$ or $=PS(OR)$ where R is an alkyl group containing from 1 to 5 and preferably from 1 to 3 carbon atoms, the phenyl radical, the o-, m- or p-nitrophenyl radical;

Alk represents an alkylene group containing from 2 to 4 carbon atoms;

$R^1$ represents an alkyl group containing from 1 to 5 carbon atoms, the benzyl or the phenyl group;

$R^2$ represents an alkyl group containing from 1 to 5 carbon atoms, a cycloalkyl group containing from 5 to 8 carbon atoms, the phenyl group, the benzyl group or the 2-methoxyethyl group, $R^1$ and $R^2$ optionally being the same or different;

n=0, 1 or 2; and, x (as the number of residual valencies of the groups Z) is the number 3, 2 or 1.

The new compounds can be obtained without difficulty in substantially quantitative yields. The process by which they are produced is characterised in that a phosphorus halide corresponding to the general formula $$Z-Hal_x \quad (II)$$

in which

Z is as defined above;

Hal represents chlorine or bromine, particularly chlorine; and, x is again the number 3, 2 or 1 is reacted with a mercaptosilane corresponding to the general formula $$R_n^1(R^2O)_{3-n}-Si-Alk-SH \quad (III)$$

in which

Alk, $R^1$, $R^2$ and n are as defined above.

The bridge member Alk represents in particular ethylene, n-propylene (trimethylene), 1-methylethylene, 2-methylethylene, n-butylene (tetramethylene), 1-methyl propylene, 2-methyl propylene and 3-methyl propylene, preferably n-propylene.

To remove the hydrogen halide formed during the reaction, it is of advantage to add to the reaction mixture a known hydrogen halide acceptor, such as the organic bases aniline, pyridine, triethylamine or another known tertiary amine, preferably in an equimolecular quantity.

The reaction is best carried out in an inert, anhyrous or substantially anhydrous organic solvent in which the amine hydrohalide formed is insoluble. Suitable solvents are, for example, petroleum ether, hexane, heptane, octane, etc., cyclohexane, aromatic hydrocarbons, such as benzene, toluene, xylene, or ethers such as diethyl ether, di-n-propyl ether, di-i-propyl ether, ethylpropyl ether, etc., and inter alia tetrahydrofuran and dioxane.

It is also of advantage to carry out the reaction in the absence of air and/or moisture (water) in order to avoid secondary reactions. For example, the reaction may be carried out in the presence of a dry inert gas, such as nitrogen or a noble gas, e.g., argon or helium. These new compounds are generally produced by initially introducing a mixture of the mercaptosilane and the above-mentioned acceptor into a solvent, cooling the mixture to room temperature or even to a lower temperature and adding the phosphorus halide dropwise. On completion of the addition, the reaction is completed at room temperature or at a higher temperature. However, it can also be of advantage to work under reflux at boiling temperature or at a temperature increasing to the boiling temperature.

On completion of the reaction, the reaction mixture is optionally cooled, the solid precipitated is separated off and the solvent is removed from the remaining solution, preferably under reduced pressure or by distillation. The residual end product may be used directly, i.e., without purification.

The starting compounds corresponding to formula (II) include, for example, trichlorophosphine, dichloromethyl phosphine, dichloroethyl phosphine, dichloro-i-propyl phosphine, dichloro-n-propyl phosphine, dichloro-i- and -n-butylphosphine, dichloro-i- and -n-pentyl phosphine, dichlorophenyl phosphine, monochlorodiphenyl phosphine, monochlorodimethyl phosphine, monochloro diethyl phosphine, monochlorodi-n- and -i-propyl phosphine, monochloro dibutyl phosphine, monochloro dipentyl phosphine, o-nitrophenyl dichloro phosphine, as well as the analogous bromophosphines, e.g., dibromomethyl phosphine, dibromomonopentyl phosphine, also trichlorophosphine oxide, trichlorophosphine sulphide, tribromophosphine oxide, tribromophosphine sulphide, O,O'-dimethyl phosphoric acid chloride, O,O'-diethyl phosphoric acid chloride, O,O'-dipropyl phosphoric acid chloride, O,O'-diisopropyl phosphoric acid chloride, O,O'-dibutyl phosphoric acid chloride, O,O'-di-sec. butyl phosphoric acid chloride, O,O'-dipentyl phosphoric acid chloride, O,O'-dimethyl phosphoric acid bromide, O,O'-diethyl phosphoric acid bromide, O,O'-dipropyl phosphoric acid bromide, O,O'-dibutyl phosphoric acid bromide, O,O'-dipentyl phosphoric acid bromide, O,O'-diphenyl phosphoric acid chloride, O-methyl-O'-phenyl phosphoric acid chloride, O,O'-bis(4-nitrophenyl) phosphoric acid bromide, dichlorophosphorous acid methyl ester, ethyl ester and so on up to the pentyl ester, dichlorophosphorous acid phenyl ester, dibromophosphorous acid-4-nitrophenyl ester, dichlorophosphorous acid-2-nitrophenyl ester, chlorothiophosphoric acid dimethyl ester, chlorothiophosphoric acid diethyl ester, chlorothiophosphoric aciddiphenyl ester, chlorothiophosphoric acid-di(2-nitrophenyl) ester, chlorothiophosphoric acid-di-i-propyl ester, bromothiophosphoric acid-di-n-propyl ester, chlorothiophosphoric acid-di-i-butyl ester, chlorothiophosphoric acid di-n-pentyl ester, dichlorothiophosphoric acid methyl ester, dichlorothiophosphoric acid ethyl ester, dichlorothiophosphoric acid -n-pentyl ester, dichlorothiophosphoric acid-n-propyl ester, dichlorothiophosphoric acid-n-butyl ester, dichlorothiophosphoric acid phenyl ester, dibromothiophosphoric acid-4-nitrophenyl ester, dichlorophosphoric acid-4-nitrophenyl ester, dichlorophosphoric acid phenyl ester, dichlorophosphoric acid methyl ester, dichlorophosphoric acid ethyl ester, dichlorophosphoric acid-n-propyl ester, dichlorophosphoric acid-n-butyl ester, dichlorophosphoric acid-n-pentyl ester, chlorophosphorous acid diethyl ester, chlorophosphorous acid, chlorophosphorous acid dimethyl ester, chlorophosphorous acid di-n-propyl ester, chlorophosphorous acid di-n-butyl ester, chlorophosphorous acid di-n-pentyl ester, chlorophosphorous acid di-(2-nitrophenyl) ester, chlorophosphoric acid diphenyl ester and the corresponding bromine compounds. The above-mentioned dihalogen and trihalogen compounds are preferred.

As mentioned above, the phosphorus halides II are reacted with mercaptosilanes III. The mercaptosilanes III include in particular 3-mercaptopropyl trimethoxysilane, 3-mercaptopropyl triethoxy silane, 3-mercaptopropyl tri-n-propoxy silane, 3-mercaptopropyl tri-n-butoxy silane, and so on up tp 3-mercaptopropyl tri-i- and -n-pentoxy silane, 3-mercaptopropyl tricyclopentoxy silane, 3-mercaptopropyl tricyclohexyloxy silane, and so on up to 3-mercaptopropyl tricyclooctoxy silane, 3-mercaptopropyl-tris-(2-methoxyethoxy)silane, 3-mercaptopropyl triphenoxy silane and 3-mercaptopropyl tribenzyloxy silane. Although any silanes containing mercapto groups may be subjected to the reaction according to the invention, the above-mentioned mercapto trisoxy silanes, i.e., those containing three identical oxy groups and/or an alkylene intermediate linking group Alk with 3 carbon atoms, are preferred, particularly because the oxy groups and particularly the lower alkoxy groups ($C_1$–$C_3$) may be regarded as effective filler-reactive groups for the most important application for which the new compounds are intended, i.e., in rubber mixtures containing light fillers, such as silica fillers.

Other mercapto silanes III containing at least one oxy group are 2-mercaptoethyl trimethoxy silane, 2-mercapto-2'-methylethyl trimethoxy silane, 2-mercapto-1'-methylethyl methoxy dimethyl silane, 3-mercaptopropyl diethoxy ethyl silane, 3-mercaptopropyl propoxy diethoxy silane, 3-mercaptopropyl propoxy dipropyl silane, 3-mercaptopropyl-2-methyl propoxy methoxy phenoxy silane, 3-mercaptopropyl-bis-(2-methoxyethoxy)-ethoxy silane, 3-mercapto-2-methylpropyl cyclohexoxy diethoxy silane, 3-mercaptopropyl phenyl diethoxy silane, 3-mercaptopropyl dibenzyloxy methyl silane, 3-mercapto-1-methylpropyl di-n-pentoxy methyl silane and 3-mercapto-n-butyl diethoxy phenoxy silane.

The radical $R^1$ in formula (III) may be present once or twice and represents in particular methyl, ethyl, n-propyl, i-propyl, n-butyl, i-butyl, 1-methylpropyl, n-pentyl, 1-methyl butyl, 2-methyl butyl, 3-methyl butyl, benzyl and phenyl. $R^1$ preferably represents methyl, ethyl, n-propyl, i-propyl and phenyl. By contrast, $R^2$ must be present in the molecule once, twice or, preferably, three times and represents an alkyl group which is fastened to silicon through oxygen. In particular, $R^2$ represents methyl or ethyl, but also i-propyl, n-propyl, n-butyl, i-butyl, 1-methyl butyl, 2-methyl butyl, 3-methyl butyl, cyclopentyl, cyclohexyl, cycloheptyl, cyclooctyl, phenyl, benzyl and 2-methoxy ethyl.

The new silanes are produced in according with the following equation:

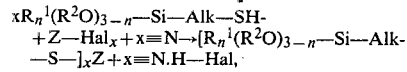

in which Z, Alk, $R^1$, $R^2$, n and x are as defined above.

The reaction is carried out for example as follows. The mercaptosilane, the solvent for the mercaptosilane and triethylamine (for example, 1 mole per mole of silane) are initially introduced into a three necked flask of adequate size which is provided with a dropping funnel, reflux condenser and stirrer and into which nitrogen is continuously introduced, and cooled to a temperature between 0° C. and room temperature.

Phosphorus halide dissolved in the same solvent is then added dropwise with stirring and cooling. On completion of the addition, the reaction mixture is left to react for a while without heating and is then heated for about 1 hour to reflux temperature.

After cooling to room temperature and separation of the aminohydrohalide formed by filtration, the solvent is distilled off under reduced pressure by means of, for example, a rotary evaporator.

The new phosphorus- and sulphur-containing silanes are more or less viscous, colourless to pale yellowish liquids which, in general, are highly sensitive to hydrolysis and cannot be distilled under normal conditions. However, it has been found that they can be successfully used without rectification for the purpose envisaged. The structure of the new compounds was confirmed by elemental analysis, infrared and nuclear resonance spectroscopy.

In addition to the compounds mentioned in the working examples, other compounds within the invention include for example tetrathiophosphoric acid-tris-[3-n-pentoxysilylpropyl ester], tetrathiophosphoric acid-tris-[3-cyclopentoxysilylpropyl ester], tetrathiophosphoric acid-tris-[3-cyclooctoxysilylpropyl ester], tetrathiophosphoric acid-tris-[3-phenoxysilylpropyl ester], tetrathiophosphoric acid-tris-[3-benzyloxysilylpropyl ester], trithiophosphoric acid-S,S',S"-tris-(3-n-pentoxysilylpropyl ester), trithiophosphoric acid-S,S',S"-tris-(3-cyclopentoxysilylpropyl ester), trithiophosphoric acid-S,S',S"-tris-(3-cyclooctoxysilylpropyl ester), trithiophosphoric acid-S,S',S"-tris-(3-phenoxysilylpropyl ester), trithiophosphoric acid-S,S',S"-tris-(3-benzyloxysilylpropyl ester), trithiophosphoric acid-S,S',S"-tris-(3-2'-methoxyethoxysilylpropyl ester), tetrathiophosphoric acid-tris-(3-2'-methoxyethoxysilylpropyl ester), tetrathiophosphoric acid-tris-(3-di(methoxy)ethoxysilylpropyl ester), trithiophosphoric acid-S,S',S"-tris-(3-methoxy di(ethoxy)silylpropyl ester), compounds of the formulae:

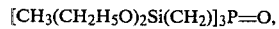

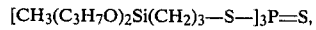

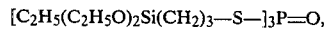

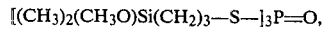

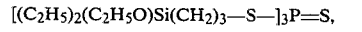

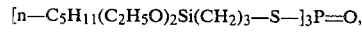

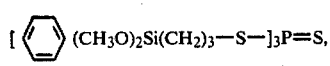

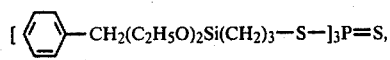

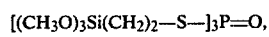

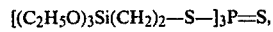

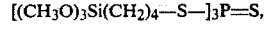

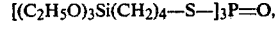

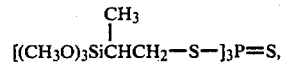

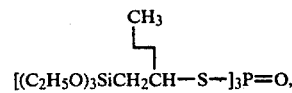

(CH₃O)₃Si(CH₂)₃—S—P(S)(OCH₃)₂, (C₂H₅O)₃Si(CH₂)₃—S—P(S)(OC₂H₅)₂, (C₂H₅O)₃Si(CH₂)₃—S—P(O)(OCH₃)₂, (C₂H₅O)₃Si(CH₂)₃—S—P(O)(O-n-C₃H₇)₂, (C₃H₇O)₃Si(CH₂)₃—S—P(S)(OC₂H₅)₂, (C₂H₅O)₃Si(CH₂)₃—S—P(S)(O—n—C₅H₁₁)₂, (CH₃O)₃Si(CH₂)₃—S—P(O)(O—n—C₅H₁₁)₂,

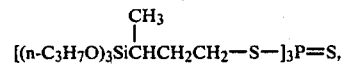

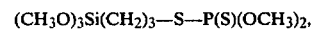

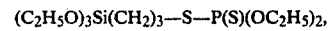

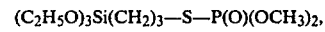

[(CH₃O)₃Si(CH₂)₃—S—]₃P,

[(C₂H₅O)₃Si(CH₂)₃—S—]₃P,

[(n—C₃H₇O)₃Si(CH₂)₃—S—]₃P,

[(n—C₅H₁₁O)₃Si(CH₂)₃—S—]₃P,

[(CH₃O)₃Si(CH₂)₃—S—]₂PCH₃,
[(C₂H₅O)₃Si(CH₂)₃—S—]₂PC₂H₅, (CH₃O)₃Si(CH₂)₃—S—P(OC₂H₅)₂,
(C₂H₅O)₃Si(CH₂)₃—S—P(OCH₃)₂, (C₂H₅O)₃Si(CH₂)₃—S—P(O—n—C₃H₇)₂, (C₂H₅O)₃Si(CH₂)₃—S—P(O—i—C₅H₁₁)₂,

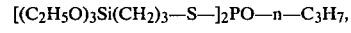

[(CH₃O)₃Si(CH₂)₃—S—]₂POCH₃,

[(CH₃O)₃Si(CH₂)₃—S—]₂POC₂H₅,

[(CH₃O)₃Si(CH₂)₃—S—]₂PO—i—C₃H₇,

[(CH₃O)₃Si(CH₂)₃—S—]₂PO—n—C₄H₉,

[(CH₃O)₃Si(CH₂)₃—S—]₂PO—n—C₅H₁₁,

[(C₂H₅O)₃Si(CH₂)₃—S—]₂POCH₃,

[(C₂H₅O)₃Si(CH₂)₃—S—]₂POC₂H₅,

[(C₂H₅O)₃Si(CH₂)₃—S—]₂PO—n—C₃H₇,

[(CH₃O)₃Si(CH₂)₃—S—]₂P(O)OCH₃,

[(C₂H₅O)₃Si(CH₂)₃—S—]₂P(O)OC₂H₅,

[(C₂H₅O)₃Si(CH₂)₃—S—]₂P(O)O—n—C₃H₇,

[(C₂H₅O)₃Si(CH₂)₃—S—]₂P(O)O—n—C₅H₁₁,

[(CH₃O)₃Si(CH₂)₃—S—]₂P(S)OCH₃,

[(CH₃O)₃Si(CH₂)₂—S—]₂P(S)OC₂H₅,

[(C₂H₅O)₃Si(CH₂)₃—S—]₂P(S)OCH₃,

[n—C₃H₇O)₃Si(CH₂)₄—S—]₂P(S)OCH₃.

The process can comprise, consist essentially of or consist of the steps set forth and the compositions can comprise, consist essentially of or consist of the materials set forth.

Unless otherwise indicated all parts and percentages are by weight.

DESCRIPTION OF THE PREFERRED EMBODIMENTS

PRODUCTION EXAMPLES

EXAMPLE 1

294 g of 3-mercaptopropyl trimethoxy silane and 200 ml of triethylamine were initially introduced into 500 ml of petroleum ether (petrol mixture boiling at 50° to 70° C.). 85 g of trichlorophosphine sulphide (SPCl₃) dissolved in 150 ml of petroleum ether were then added dropwise over a period of 1 hour, the reaction temperature being kept by cooling at around 20° C. The reaction mixture was then left standing overnight at room temperature and subsequently heated for 1 hour to reflux temperature. The reaction was substantially quantitative. Tetrathiophosphoric acid-tris-[3-trimethoxysilylpropyl ester] corresponding to the formula [(CH₃O)₃Si—(CH₂)₃—S—]₃P=S was obtained in a yield of 319,4 g, its elemental analysis being as follows (in percent by weight):

|  | C | H | Si | S | P |
|---|---|---|---|---|---|
| Observed | 31.82 | 6.52 | 12.73 | 18.50 | 4.50 |
| Calculated | 31.31 | 6.99 | 12.98 | 19.76 | 4.77 |

The compound has a refractive index $n_D^{20}$ of 1.4971. The yield corresponded to 98.5% of the theoretical.

EXAMPLE 2

Following the procedure of Example 1, 233 g of 3-mercaptopropyl triethoxy silane and 98.8 g of triethylamine were initially introduced into 400 ml of petroleum ether (50° to 70° C.) in the reaction vessel, followed by the dropwise addition of 50 g of $OPCl_3$ in 200 ml of the petroleum ether (addition time 1 hour, cooling, reaction temperature 20° C.). The reaction mixture was left to react for 1 hour at reflux temperature. Trithiophosphoric acid-S,S',S''-tris-(3-triethoxysilylpropyl ester) corresponding to the formula $[(C_2H_5O)_3Si(CH_2)_3-S-]_3PO$ was obtained in a yield of 242.6 g, its elemental analysis producing the following results:

|  | C | H | Si | S | P |
|---|---|---|---|---|---|
| Observed | 41.83 | 8.14 | 10.67 | 13.42 | 3.88 |
| Calculated | 42.71 | 8.36 | 11.09 | 12.67 | 4.08 |

Refractive index $n_D^{20} = 1.4692$. Yield: 98.0% of the theoretical.

EXAMPLE 3

Following the procedure of Example 2, 610.7 g of trithiophosphoric acid-S,S',S''-tris-(3-trimethoxysilylpropylester) or alternative name [tris-(trimethoxysilyl-trimethylene-thio)-phosphine oxide] corresponding to the formula $[(CH_3O)_3Si(CH_2)_3-S-]_3PO$, were produced from trichlorophosphine oxide and 3-trimethoxysilyl propyl mercaptan in a 1-molar batch. Elemental analysis produced the following results:

|  | C | H | Si | S | P |
|---|---|---|---|---|---|
| Observed | 33.43 | 6.97 | 12.04 | 14.62 | 4.65 |
| Calculated | 34.16 | 7.17 | 13.31 | 15.20 | 4.89 |

Refractive index $n_D^{20} = 1.4769$. Yield 96.5% of the theoretical.

EXAMPLE 4

Following the procedure of Example 1, 767.5 g of tetrathiophosphoric acid-tris-(3-triethoxysilyl-propyl ester) or alternative name [tris-(triethoxysilyl-trimethylene-thio)-phosphine sulfide] corresponding to the formula $[(C_2H_5O)_3Si(CH_2)_3-S-]_3PS$ were obtained from $SPCl_3$ and 3-mercaptopropyl triethoxy silane in a 1-molar batch. Elemental analysis produced by the following results:

|  | C | H | Si | S | P |
|---|---|---|---|---|---|
| Observed | 39.59 | 8.12 | 9.94 | 17.47 | 4.22 |
| Calculated | 41.83 | 8.19 | 10.87 | 16.54 | 3.99 |

Refractive index $n_D^{20} = 1.4852$. Yield 99.0% of the theoretical.

EXAMPLE 5

Following the procedure of Example 4, 971.3 g of tetrathiophosphoric acid-tris-(3-tri-n-butoxysilylpropyl ester) or alternative name [tris-(tri-n-butoxysilyl-trimethylene-thio)-phosphine sulphide] corresponding to the formula $[(C_4H_9O)_3Si(CH_2)_3-S-]_3PS$ were produced from $SPCl_3$ and 3-mercaptopropyl tri-n-butoxy silane in a 1-molar batch. Elemental analysis produced the following results:

|  | C | H | Si | S | P |
|---|---|---|---|---|---|
| Observed | 49.27 | 9.30 | 7.60 | 12.16 | 3.52 |
| Calculated | 52.59 | 9.71 | 8.20 | 12.48 | 3.01 |

Refractive index $n_D^{20} = 1.4741$. Yield 94.5% of the theoretical.

EXAMPLE 6

Following the procedure of Examples 2 and 3, 948.0 g of thiophosphoric acid-S,S,S-tris-3-tributoxysilyl propyl ester [=tris-(tri-n-butoxysilyl-trimethylene-thio)-phosphine oxide] corresponding to the formula $[(C_4H_9O)_3Si(CH_2)_3-S-]_3PO$ were produced from $OPCl_3$ and 3-mercaptopropyl tri-n-butoxy silane in a 1-molar batch. Elemental analysis produced the following results:

|  | C | H | Si | S | P |
|---|---|---|---|---|---|
| Observed | 52.24 | 8.67 | 7.99 | 9.85 | 2.87 |
| Calculated | 53.42 | 9.86 | 8.33 | 9.51 | 3.06 |

Refractive index $n_D^{20} = 1.4561$. Yield 93% of the theoretical.

EXAMPLE 7

Following the procedure of Example 3, chlorothiophosphoric acid diethyl ester $[ClP(S)(OC_2H_5)_2]$ was reacted with 3-mercaptopropyl trimethoxy silane in a 1-molar batch. The solvent used was tetrahydrofuran. After the thiophosphoric acid compound had been added dropwise, the reaction mixture was left to react for 3 hours at reflux temperature. O,O'-diethyl dithiophosphoric acid-(3-trimethoxysilyl-propyl ester) (alternative name: trimethoxy silyl trimethylene thiophosphoric acid diethyl ester) corresponding to the formula $(CH_3O)_3Si(CH_2)_3-S-P(S)(OC_2H_5)_2$ was obtained in a yield of 345 g. Elemental analysis of this ester produced the following results:

|  | C | H | Si | S | P |
|---|---|---|---|---|---|
| Observed | 31.76 | 8.39 | 7.65 | 17.87 | 10.03 |
| Calculated | 34.47 | 7.23 | 8.06 | 18.4 | 8.89 |

Refractive index: $n_D^{20} = 1.4829$. Yield 99.0% of the theoretical.

EXAMPLE 8

Following the procedure of Example 7, 311.6 g of O,O'-diethyl thiophosphoric acid-S-(3-trimethoxysilyl propyl ester) (alternative name: trimethoxysilyl trimethylene thiophosphoric acid diethyl ester) corresponding to the formula $OP(OC_2H_5)_2S-(CH_2)_3Si(OCH_3)_3$ were produced from chlorophosphoric acid diethyl ester $OP(OC_2H_5)_2Cl$ and 3-mercaptopropyl trimethoxy silane in a 1-molar batch. As in the preceding examples, the hydrochloride of the triethylamine used as acid acceptor was formed as secondary product. Elemental analysis of the new ester produced the following results:

|            | C     | H    | Si   | S    | P    |
|------------|-------|------|------|------|------|
| Observed   | 35.46 | 8.74 | 7.91 | 9.26 | 9.82 |
| Calculated | 36.13 | 7.58 | 8.45 | 9.65 | 9.31 |

Refractive index: $n_D^{20} = 1.4561$. Yield 93.8% of the theoretical.

The corresponding triethoxy silyl compound having the refractive index $n_D^{20} = 1.4591$ was similarly produced.

EXAMPLE 9

Following the procedure of Example 1, 709.0 g of trithiophosphorous acid-tris-(3-triethoxysilyl propyl ester) (alternative name: [tris-(triethoxysilyl-trimethylene-thio)-phosphine]) in the form of a liquid were obtained from a solution of 715 g (3 moles) of 3-mercaptopropyl triethoxy silane in petroleum ether (1000 ml) with addition of 3 moles of triethylamine (303 g) dissolved in 500 ml of petroleum ether (50°–70° C.) by reaction with 137 g of phosphorous trichloride (dissolved in 350 ml of petroleum ether). Elemental analysis produced the following results:

|            | C     | H    | Si    | S     | P    |
|------------|-------|------|-------|-------|------|
| Observed   | 42.0  | 8.49 | 11.94 | 12.32 | 4.46 |
| Calculated | 42.63 | 8.54 | 11.34 | 12.94 | 4.17 |

Formula: $P[S-(CH_2)_3Si(OC_2H_5)_3]_3$. Refractive index $n_D^{20} = 1.4780$. Yield 95.4% of the theoretical.

EXAMPLE 10

Following the procedure described in Examples 1 and 9, 609.5 g of trithiophosphorous acid-tris-(3-trimethoxysilyl propyl ester) [alternative name: tris-(trimethoxysilyl trimethylene thio)-phosphine] were produced from phosphorus trichloride and 3-mercaptopropyl trimethoxy silane in a 1-molar batch. Elemental analysis produced the following results:

|            | C     | H    | Si    | S     | P    |
|------------|-------|------|-------|-------|------|
| Observed   | 33.46 | 7.17 | 14.09 | 14.29 | 5.1  |
| Calculated | 35.04 | 7.35 | 13.66 | 15.59 | 5.02 |

Refractive index $n_D^{20} = 1.4909$. Yield 98.8% of the theoretical.

The new sulphur- and phosphorus-containing organosilicon compounds are suitable for use as corrosion inhibitors, as additives to lubricant compositions and, in particular, as adhesion promoters in rubber mixtures based on natural or synthetic rubbers or mixtures of rubbers which contain as fillers silicate-based fillers and, optionally, carbon black and also sulphur and inter alia the usual vulcanisation accelerators. In the context of the invention, the expression "silicate-based filler" is used in the broad sense and applies to light fillers which consist of silicates, contain silicates and/or comprise silicates in the broadest sense in chemically bound form and which are compatible with rubbers or can be worked into rubber mixtures. The silicate-based fillers include in particular highly disperse silicas (produced by precipitation from solutions of silicates, by the hydrolytic and/or oxidative reaction of volatile silicon halides at high temperatures or by an arc process), synthetic silicates, natural silicates such as kaolins, clays and asbestos, and also natural silicas such as, for example, quartz and kieselguhr, glass fibres and glass fibre products.

The above-mentioned silicate-based fillers are preferably used in quantities of from about 10 parts by weight or, optionally, even less up to about 250 parts by weight, based on 100 parts by weight of the rubber.

The rubber mixture can be produced with one or more, in a given case oil-extended, natural and/or synthetic rubbers, preferably diene elastomers as for example polybutadiene, polyisoprene, e.g., cis-polyisoprene, butadiene-styrene copolymer, butadiene-acrylonitrile copolymer, polymerised 2-chlorobutadiene, also butyl rubber, halogenated butyl rubber such as chlorinated butyl rubber, brominated butyl rubber as well as other known diene rubbers as for example, non-conjugated dienes and also non-conjugated polyenes, e.g., ethylene-propylene-cyclooctadiene, ethylene-propylene-norbornadiene, ethylene-propylene dicyclo-pentadiene and ethylene-propylene-cyclododecatriene. Also there can be used trans-polypentenamer, carboxy or epoxy rubbers and the like known elastomers. The chemical derivatives of natural rubber and modified natural rubber can also be used in the invention.

The new organosilicon compounds are usually employed in an amount of 0,1 to 50 parts per 100 parts of rubber.

The new organosilicon compounds were tested in a rubber mixture of the following composition (quantities in parts by weight):

| Mixture constituents | Quantities |
|---|---|
| Natural rubber (ribbed smoked sheets I, Defo hardness 1000, with 0.25 zinc pentachlorothiophenate added) | 100.0 |
| Finely divided precipitated silica filler (Degussa's Ultrasil ® VN 3) | 40.0 |
| Zinc oxide (red seal quality) | 3.0 |
| Stearic acid | 5.0 |
| Silane (various, corresponding to the invention) | 2.0 |
| Di-2-benzothiazyl disulphide | 0.8 |
| Diphenyl guanidine | 2.0 |
| Sulphur | 2.5 |

The mixtures were produced on a roll mill. Testing of the properties of the unvulcanised rubber mixtures which contained the above-mentioned quantities of organosilicon compounds corresponding to the preceding production examples showed a slight reduction in the Mooney scorch and Mooney cure times in relation to the reference mixture (no silane added) coupled with the required distinct reduction in the Mooney plasticity values (also known as Mooney viscosity, measured at 100° C. in accordance with DIN 53 523) from 80 (for the reference mixture) to a figure quoted in the following list for the mixtures containing added silane corresponding to the production examples for these silanes:

| Silane added corresponding to production Example No. | Mooney plasticity ML 4 |
|---|---|
| 1 | 45 |
| 2 | 53 |

| Silane added corresponding to production Example No. | Mooney plasticity ML 4 |
|---|---|
| 3 | 40 |
| 4 | 39 |
| 5 | 44 |
| 6 | 47 |
| 7 | 56 |
| 8 | 52 |
| 9 | 41 |
| 10 | 34 |

This marked reduction in the viscosities of the unvulcanised rubber mixtures represents an important advantage so far as processing is concerned. The addition of the silanes according to the invention to rubber mixtures containing silicate-based and/or silica fillers increases the moduli of the vulcanisate very considerably to an extent which enables the vulcanisates to be used for numerous practical applications. The modulus-increasing effect of the organosilanes (reinforcing effect) is a measure of their activity in rubber.

Thus, the modulus 300 (stress value at 300% elongation measured in kp/cm$^2$) of a vulcanisate of the above-described rubber mixture increases from 59 for the above-mentioned reference mixture to the following values for the vulcanisates of rubber mixtures containing the silanes corresponding to the production examples (vulcanisation 20 minutes at 145° C.):

| Silane corresponding to production Example No. | Modulus 300 in kp/cm$^2$ |
|---|---|
| 1 | 108 |
| 2 | 105 |
| 3 | 107 |
| 4 | 101 |
| 5 | 90 |
| 6 | 95 |
| 9 | 103 |
| 10 | 105 |
| Reference mixture (no silane) | 59 |

Accordingly, the silanes according to the invention are effective reinforcing additives in rubber mixtures which contain silicate-based fillers, including silica fillers, of all known origins in quantities of from about 10 to 250 parts by weight and preferably in quantities of up to 150 parts by weight. In addition, these mixtures based on natural and/or synthetic rubbers may also contain rubber-grade carbon blacks in quantities of from 0.1 to 150 parts by weight, based on 100 parts by weight of rubber. In addition to the cross-linking system, the rubber mixtures may contain the other usual mixture constituents known from rubber technology, such as antiagers, antifatigue, agents, antiozonants, processing aids, in quantities of from 0.5 to 10 parts by weight, based on 100 parts by weight of rubber; also dyes, pigments, plasticisers, blowing agents, waxes, extenders such as, for example, sawdust; organic acids such as stearic acid, benzoic acid or policylic acid in quantities of from 0.2 to 10 parts by weight, based on 100 parts by weight of rubber; metal oxides such as zinc oxide or lead oxide in quantities of from 0.2 to 10 parts by weight, based on 100 parts by weight of rubber; activators such as, for example, triethanolamine, polyethylene glycol or hexane triol, in quantities of from 0.5 to 10 parts by weight, based on 100 parts by weight of rubber. The above-mentioned cross-linking system preferably consists of sulphur and/or sulphur donors in total quantities of from 0.1 to 8 parts by weight, based on 100 parts by weight of rubber, plus one or more accelerators in quantities of from 0.2 to 8 parts by weight, based on 100 parts by weight of rubber, or of metal oxides, such as magnesium or zinc oxide, in quantities of from 1 to 15 parts by weight, based on 100 parts by weight of rubber, or of peroxides in the usual quantities.

The rubber mixtures are produced, moulded and vulcanised by the methods and with the apparatus normally used in the rubber industry (cf. "Kautschuk-Handbuch" by S. Bostrom, Verlag Berliner Union, Stuttgart, 1959, or A. S. Craig, "Rubber Technology," London 1963).

The rubber mixtures are suitable for the production of, for example, technical rubber articles such as cable sheaths, hoses, drive belts, V-belts, conveyor belts, roller coatings, tire treads, carcasses and side walls for motor vehicles, particularly motor cars, earth movers and trucks, cross-country tires, soling materials for shoes, sealing rings, damping elements and many other products. The new rubber mixtures have also proved to be suitable for adhesion mixtures for improving the adhesion of rubbers to reinforcing materials or reinforcing supports particularly fibres, fibre-based materials and wires of, for example, glass, metal (zinc-plated or brass-plated steel cord) and textile materials (polyamide or polyester fabrics and the like).

What is claimed is:

1. A composition comprising (a) a compound of the formula

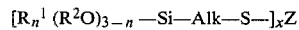

$$[R_n^1 (R^2O)_{3-n} -Si-Alk-S-]_x Z$$

in which Z has the meanings =PO, =PS, =P, =PR, —P(R)$_2$, —P(OR)$_2$, =P(OR), —PO(OR)$_2$, —PS(OR)$_2$, =PO(OR) or =PS(OR) where R is an alkyl group containing from 1 to 5 carbon atoms, the phenyl radical, the nitrophenyl radical;

Alk is an alkylene group containing from 2 to 4 carbon atoms;

R$^1$ is an alkyl group containing from 1 to 5 carbon atoms, the benzyl group or the phenyl group;

R$^2$ represents an alkyl group containing from 1 to 5 carbon atoms, a cycloalkyl group containing from 5 to 8 carbon atoms, the phenyl group, the benzyl group or the 2-methoxy ethyl group;

n=0, 1 or 2; and x=3, 2 or 1.

(b) a vulcanizable rubber and (c) a siliceous filler.

2. A composition according to claim 1 wherein in the compound (a) Z is =PO, =PS, =P, =PR, —P(OR$_2$), =P(OR), —PS(OR)$_2$, =PO(OR) or =PS(OR).

3. A composition according to claim 1 wherein in the compound (a) Z is =PS.

4. A composition according to claim 1 wherein in the compound (a) Z is =PO.

5. A composition according to claim 1 wherein in the compound (a) Z is —PS(OR)$_2$.

6. A composition according to claim 1 wherein in the compound (a) Z is —PO(OR)$_2$.

7. A composition according to claim 1 wherein in the compound (a) Z is =PO, =PS, =P, =PR, —P(OR)$_2$, =P(OR), —PO(OR)$_2$, —PS(OR)$_2$, =PO(OR) or =PS(OR).

8. A composition according to claim 7 where n is 0.

9. A composition according to claim 8 where R$^2$ is alkyl of 1 to 5 carbon atoms.

10. A composition according to claim 8 wherein $R^2$ is alkyl of 1 to 3 carbon atoms.

11. A composition according to claim 9 wherein Z is $\equiv$PS, $\equiv$PO, —PS(OR)$_2$ or —PO(OR)$_2$.

12. A composition according to claim 1 where $R^1$ is alkyl of 1 to 5 carbon atoms.

13. A composition according to claim 9 wherein Alk is trimethylene.

14. A composition according to claim 7 free from carbon black.

15. A composition according to claim 14 including carbon black.

16. A composition according to claim 1 wherein the polymer is sulphur curable and the composition includes sulphur.

17. A composition according to claim 1 wherein the siliceous filler is silica.

* * * * *